United States Patent
Klotz et al.

(10) Patent No.: US 7,203,353 B2
(45) Date of Patent: Apr. 10, 2007

(54) METHOD AND APPARATUS FOR PROCESSING A COMPUTED TOMOGRAPHY IMAGE OF A LUNG OBTAINED USING CONTRAST AGENT

(75) Inventors: Ernst Klotz, Uttenreuth (DE); Matthias Niethammer, Moehrendorf (DE); Stefan Schaller, Fuerth (DE)

(73) Assignee: Siemens Aktiengesellschaft, Munich (DE)

( * ) Notice: Subject to any disclaimer, the term of this patent is extended or adjusted under 35 U.S.C. 154(b) by 829 days.

(21) Appl. No.: 10/075,802

(22) Filed: Feb. 14, 2002

(65) Prior Publication Data

US 2002/0114503 A1 Aug. 22, 2002

(30) Foreign Application Priority Data

Feb. 17, 2001 (DE) ................. 101 07 765

(51) Int. Cl.
*G06K 9/00* (2006.01)
(52) U.S. Cl. .................. 382/131; 382/128; 128/922

(58) Field of Classification Search ............... None
See application file for complete search history.

(56) References Cited

U.S. PATENT DOCUMENTS

| | | | | |
|---|---|---|---|---|
| 5,253,281 A | * | 10/1993 | Krauss | 378/98.12 |
| 5,351,305 A | * | 9/1994 | Wood et al. | 382/128 |
| 5,370,692 A | * | 12/1994 | Fink et al. | 128/898 |
| 5,396,418 A | * | 3/1995 | Heuscher | 378/15 |
| 5,687,208 A | | 11/1997 | Bae et al. | 378/901 |
| 5,986,662 A | * | 11/1999 | Argiro et al. | 345/424 |
| 6,083,162 A | | 7/2000 | Vining | 600/407 |
| 6,466,687 B1 | * | 10/2002 | Uppaluri et al. | 382/128 |

* cited by examiner

Primary Examiner—Bhavesh M. Mehta
Assistant Examiner—Christopher Lavin
(74) Attorney, Agent, or Firm—Schiff Hardin LLP

(57) ABSTRACT

In a method and apparatus for image processing proceeding from a computed tomography (CT) image of a lung as an original image that is registered using a contrast agent, pulmonary parenchyma pixels are determined, the pulmonary parenchyma pixels are presented in false colors, and the remaining image regions are presented in the gray scale values of the original image.

23 Claims, 5 Drawing Sheets

☐ = POINT OF THE CONTOUR
     TO BE FOUND

☐ = POINT OF THE CONTOUR
     ALREADY FOUND

■ = CURRENTLY FOUND POINT
     OF THE CONTOUR

☐ = CHECKED POINT, NO POINT
     OF THE CONTOUR

METHOD AND APPARATUS FOR PROCESSING A COMPUTED TOMOGRAPHY IMAGE OF A LUNG OBTAINED USING CONTRAST AGENT

BACKGROUND OF THE INVENTION

1. Field of the Invention

The present invention is directed to a method for image processing proceeding from a computer tomography (CT) image of a lung registered with a contrast agent, we well as a CT apparatus for the implementation of such a method.

2. Description of the Prior Art

Computed tomography is increasingly acquiring significance for the diagnosis of pulmonary embolisms. CT angiographies of the vessels in the thorax are analyzed.

For diagnosis of pulmonary embolisms (PE), a CT angiography of the lung is implemented. Contrast agent is injected into the patient with a contrast agent pump. After pausing a few seconds, a spiral CT of the lung is implemented, a stack (series) of axial images, i.e. transverse tomograms, preferably representing body slices adjacent to one another and following one another in the direction of the longitudinal patient axis are acquired. The vessels filled with contrast agent can be clearly seen in CT images on the basis of the increase in density. The diagnosis ensues with reference to the axial images. Dependent on the orientation of the vessels relative to the plane of section, vessels are presented as bright lines or bright points in the so-called lung window (central value of the window=–600 HU; width of the window=1500 HU). The overall vessel tree is tracked when "leafing " through the image stack and is checked for closures (thrombosis). Blockages or constrictions can be seen as dark matter in the vessel. Following the blockage, the vessel is no longer filled with contrast agent or is only partially filled with contrast agent and is therefore presented darker. This standard technique has the following problems:

Blockages can be overlooked;

The hemodynamic effect of the thrombosis cannot be identified;

Blockages at small vessels (sub-segmental) cannot be recognized in the CT image due to the limited resolution;

The degree of stenosis, i.e. the seriousness of the blockage, cannot be dependably determined; and Other pathological changes can be erroneously diagnosed as a thromboembolic blockage (for example, closed bronchi).

U.S. Pat. No. 5,687,209 discloses a method wherein CT images are generated with the assistance of a contrast agent, resulting in that those regions of the image wherein contrast agent is present exhibiting intensified gray scale values, whereas the other image regions are presented with the original gray tones.

U.S. Pat. No. 6,083,162 discloses generation of an interactive three-dimensional presentation of hollow organs under certain circumstances with the assistance of contrast agents, to which end the voxels belonging to the organ to be presented are separated from the rest of the image content.

SUMMARY OF THE INVENTION

An object of the invention is to provide an additional evaluation technique for CT images in the diagnosis of PE on the basis of computer tomography, which allows an enhanced diagnosis dependability. It is also an object of the invention to provide a CT apparatus suitable for these purposes.

The above object is achieved in accordance with the principles of the present invention in a method and an apparatus for processing an image obtained by computed tomography of a lung, using a contrast agent, wherein pulmonary parenchyma pixels are determined, and wherein a processed image is generated by presenting the pulmonary parenchyma pixels in false colors, and presenting the remaining image regions with gray scale values of the original image.

The pre-condition for the diagnosis of pulmonary parenchyma is created as a result of determining the pulmonary parenchyma pixels and the coloring of the pulmonary parenchyma pixels, i.e. those pixels of the original image that represent the pulmonary parenchyma, and the presentation of the pulmonary parenchyma pixels in false colors. The diagnosis of PE can be substantially assisted by the involvement of the pulmonary parenchyma, since vessel closures cause a low blood flow, or a failure of the blood flow in the following tissue and thus involve a reduction of the contrast agent enhancement in the corresponding regions of the pulmonary parenchyma. The effects of the thrombo-embolic event are made directly visible.

In contrast to the invention, changes in the pulmonary parenchyma are difficult to recognize for various reasons in the gray scale value presentation that is standard in computed tomography:

The reduction of the contrast agent enhancement under certain circumstances may be expressed in only slight changes of the HU values. Moreover, the pulmonary parenchyma is permeated by vessels and bronchi. The vessels can belong to other regions of the lung and contain contrast agent if their discharge proceeds the vessel blockage. A region that has uniformly low blood flow due to a thrombus in the vessel supplying it can therefore convey the impression in the image of a heterogeneous distribution of the HU values, with the result that this region is not perceived as having low blood flow by the observer.

Such problems cannot occur in the invention since those image regions that do not represent a pulmonary parenchyma, i.e. particularly the large vessels in the lung, are presented with the customary gray scale values.

Suspicious anatomical regions are clearly emphasized due to the presentation in false colors. For example, individual segments of the lung are often affected, these being clearly visible with the false color presentation. Since the large vessels are presented in the original gray tones within the colored pulmonary parenchyma, the radiologist can employ them as anatomical landmarks for orientation, this being especially advantageous when the diagnosis—as initially mentioned—ensues on the basis of an image stack.

In a preferred version of the invention, as first method step the pulmonary pixels, i.e. those pixels that are located within the contour to be found, are separated from the remaining image contents in the CT image using a contour finding algorithm, and all following method steps relating to the lung are applied only to the pulmonary pixels identified in this way. For determining pulmonary parenchyma pixels, bronchia and vessels are identified in an advantageous way on the basis of their HU values, and the corresponding pixels are removed from the pulmonary pixels. This is possible without further difficulty since bronchia exhibit HU values that lie below those of the pulmonary parenchyma, whereas the HU values of the vessels lie above the HU values of the pulmonary parenchyma. Thus, when the pixels representing bronchia and vessels are removed from the pulmonary pixels, the pulmonary parenchyma pixels remain. The application of a contour finding algorithm and separation of the pixels that are located within the contour to be found from the remaining image contents is also referred to below as segmentation.

So that holes or gaps that are not too large do not arise in the image, the segmentation in one version of the invention ensues such that only a proportion of pixels not exceeding a prescribable, maximum percentage proportion of pixels is removed, the removed pixels being classified as invalid pixels.

The smoothing operation ensues within a selectable filter mask, i.e. a number of pixels is selected that is involved in the smoothing operation. The average value of all pixels contained in the filter mask is allocated to the pixel in the mid-point of the filter mask. Invalid pixels do not contribute to the average value. The required minimum proportion of valid pixels among the pixels contained in the filter mask can be set. If the minimum proportion is not reached, then the pixel in the mid-point of the filter mask is set to invalid status. A determination thus can be made as to whether the holes containing the filter mask shrink by their pixels being replaced by the average value of the pixels surrounding them, or whether they grow at the expense of the valid pixels surrounding them.

In another version of the invention the image region representing pulmonary parenchyma, i.e. the pulmonary parenchyma pixels, is subjected to a smoothing operation, preferably a particularly three-dimensional, sliding averaging, which facilitates the diagnosis.

In another preferred embodiment of the invention the pulmonary parenchyma presented in false colors are superimposed on the original image presented in gray scale values, with pixels classified as invalid being replaced by the corresponding pixels of the original image presented in gray scale values. As a result, large vessels can be presented in their original gray tones within the segmented and colored lung.

In order to be able to adapt the presentation to the respective requirements, there is the possibility of subjecting the pulmonary parenchyma pixels represented in false colors and the other image regions represented in the gray scale values of the original image to windowing operations independently of one another. When a windowing of the pulmonary parenchyma pixels presented in false colors ensues, in one version of the invention the window values for the pulmonary parenchyma pixels presented in false colors are determined from the histogram of the pulmonary pixels, preferably using the center of gravity of the histogram distribution as the central value of the windowing, and the width of the window is set to a value of approximately 100 HU.

The application of the inventive method is not limited to individual original images but, according to a preferred embodiment of the invention, can be applied to original volume data of images of a number of original images, whereby image stacks can be reconstructed on the basis of such volume data or multi-planar reconstruction (MPR) can be undertaken.

In an embodiment of the invention two original images corresponding to one another are prepared, one thereof being acquired without contrast agent and one being acquired with contrast agent, for example by registering one image before the administration of contrast agent and the other being acquired after the administration of contrast agent. Both original images are processed according to one of the above-described methods, with the two processed images that are obtained being subtracted from one another.

A diagnosis that is improved compared to traditional gray scale value presentations is also assured in this way.

The color presentation can be integrated within the graphic user interface of a CT apparatus or of a work station serving the purpose of processing CT images, being integrated therein as an additional (soft) button (control element). Upon observation of a CT image in an arbitrary orientation, for example according to a multi-planar reconstruction (MPR), a switching can be undertaken between the gray scale value presentation and the color pulmonary parenchyma presentation.

DESCRIPTION OF THE PREFERRED EMBODIMENTS

Figure 1:
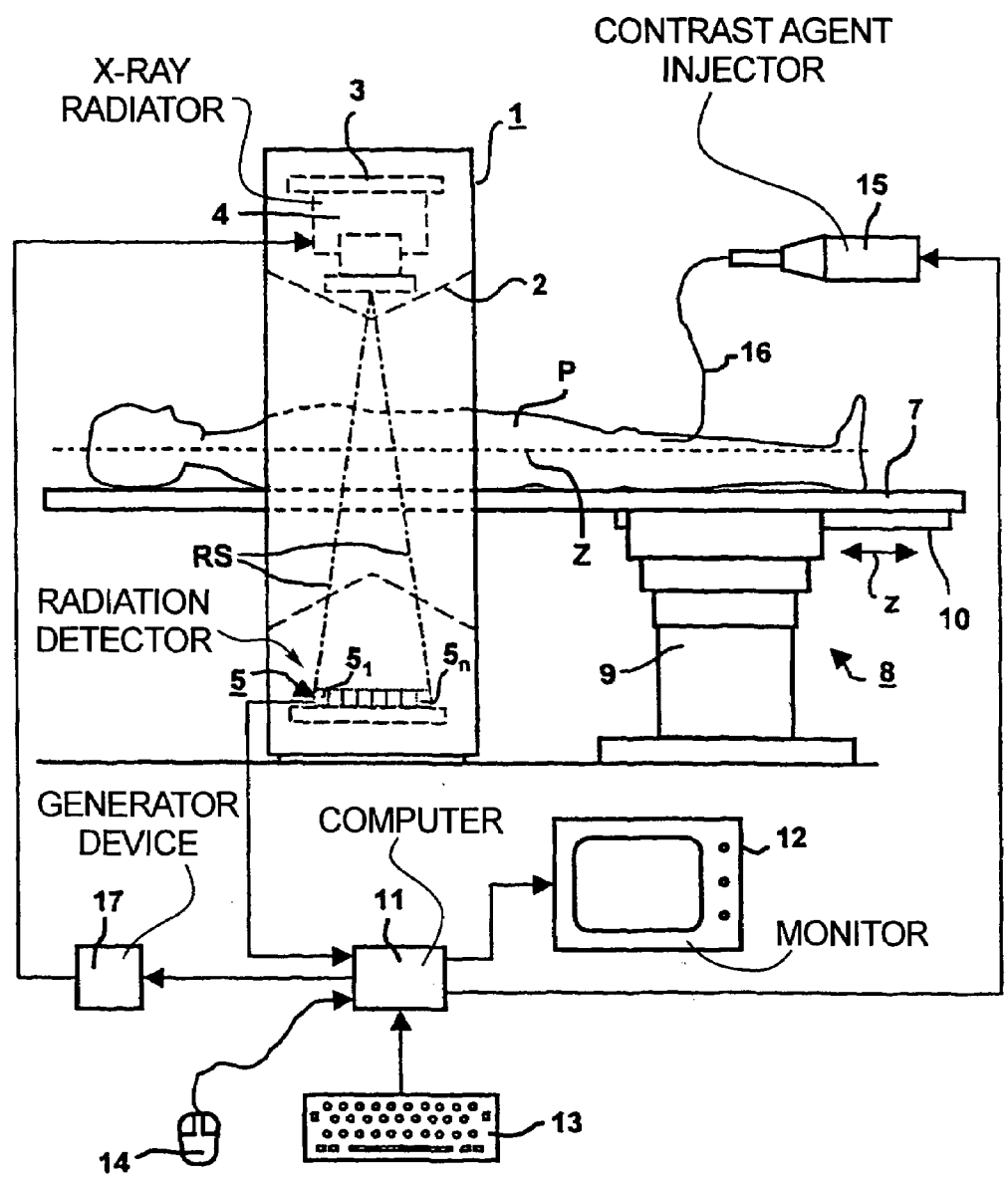
FIG. 1 illustrates an inventive CT apparatus for the implementation of the inventive method.

FIG. 1 shows an x-ray CT apparatus having a gantry 1 with a measurement opening 2 that is surrounded by a live ring 3 on which an x-ray radiator 4 and a detector system are attached. The detector system has a radiation detector fashioned in a known way and curved around an axis that preferably proceeds parallel to a system axis Z and through the focus of the x-ray radiator 4. The radiation detector 5 has a number of lines $5_1$ through $5_n$ of detector elements, each forming a row of detector elements. A pyramidal x-ray beam RS that is indicated dot-dashed and that strikes the detector 5 emanates from the x-ray radiator 4. The gantry 1 having the x-ray radiator 4 and the radiation detector 5, and at least the support plate 7 of a support mechanism provided for the acceptance of an examination subject, for example of a patient P, are adjustable relative to one another in the direction of the longitudinal axis of the support plate 7 proceeding parallel to the system axis Z. This adjustment ensues by means of a notarized drive (not shown). In the CT apparatus according to FIG. 1, this is achieved by the support plate 7 being adjustably attached to the base 9 of the support mechanism 8 with a supporting part 10. The adjustment is in the direction of the system axis Z of the support plate 7, i.e. in the direction of the double arrow referenced z.

The support plate 7 is made of a material that has low attenuation for x-rays, for example carbon fiber-reinforced plastic (CFK) or wood.

For producing computed-tomographic exposures, the gantry 1 and the support plate 7 are moved relative to one another into a position wherein the support plate 7 extends through the measurement opening 2 of the gantry 1, and the patient P lying on the support plate 7 assumes such a position relative to the gantry 1 that a region of the patient P to be examined is covered by the x-ray beam RS.

For producing exposures of one or more planar slices of the patient P, the live ring 3 together with the x-ray radiator 4 and the radiation detector 5 is rotated around the system axis Z for the registration of a plurality of projections from different directions serving for the reconstruction of one or more tomograms of one or more planar slices of the patient P while the gantry 1 and the support plate 7 retain their positions relative to one another with respect to the direction of the system axis Z. Since the detector 5 has a number of lines of detector elements, projections with respect to a plurality of slices of the patient P maximally corresponding to the number of lines $5_1$ through $5_n$ of detector 5 can be registered. The measured values corresponding to the projections, derived from one or more lines $5_1$ through $5_n$ of detector 5, are supplied to a computer 11 that uses these measured values to calculate a tomogram in a known way, but preferably a stack of tomograms that can be displayed on a display, for example a monitor 12, so it is possible to "leaf" through the stack.

A keyboard 13, a mouse 14 and/or further input devices (not shown) for operating the CT apparatus are connected to the computer 11.

In order to be able to set the x-ray dose that is required, the generator device 17 supplying the x-ray radiator 4 with the voltages and currents required for its operation is likewise controlled by the computer 11, this being indicated by a corresponding control line.

For the implementation of a spiral scan, the support plate 7 is displaced on a straight line in the direction of the system axis Z, i.e. in z-direction, with continuous rotation of the live ring 3 and with the x-ray radiator 4 activated, so that the registered projections do not refer to one or more planar slices but to one or more spiral slices. Using known methods for spiral interpolation, the computer 11 uses the measured projections acquired during the course of the spiral scan to determine calculated projections that refer to one or more desired planar slices and allow the reconstruction of corresponding tomograms. Moreover, it is possible to reconstruct threedimensional images on the basis of spiral scans since it is not only a planar slice but a volume that is scanned during the course of a spiral scan.

For examinations with a contrast agent, a contrast agent injector 15 is provided with which contrast agent can be delivered to the patient P via a cannula 16. In the exemplary embodiment, the contrast agent injector 15, as indicated by a corresponding line, is controlled by the computer 11, namely both in view of the amount of contrast agent that is supplied to the patient P per time unit as well as in view of the beginning and the end of the delivery of contrast agent.

Expediently, a reference scan is first undertaken without activating the contrast agent injector 15, this containing that region of the body of the patient P that is the subject of the examination.

The actual examination is only started after activation of the contrast agent injector 15 when an adequate concentration of contrast agent is in fact already present in the body region to be examined, for example after 30 s (seconds) in the case of an examination of the lung in conjunction with PE.

The inventive method for image processing of the CT images present in the form of stacks of images or in the form of individual images. These can be axial images or sagittal or coronal images acquired by MPR, is implemented by the computer 11 and is described in greater detail below.

The image processing ensues in five steps, namely segmentation, vessel elimination, smoothing, color coding and image superimposition.

A threshold-based algorithm is employed for segmenting the lung. Suitable algorithms are described in Pavlidis: "*Algorithms for Graphis and Image Processing*"; Springer Verlag 1982 Willi, A. Kalender, Heinz Fichte, Werner Bautz, and Martin Skalej, "Semiautomatic Evaluation Procedures for Quantitative CT of the Lung", *Journal of Computer Assisted Tomography*, 15 (2) :248–255. The user can prescribe a threshold, usually −300 HU. In order to achieve high function dependability, the algorithm was adapted to the specific conditions existing given pulmonary parenchyma.

Figure 2:
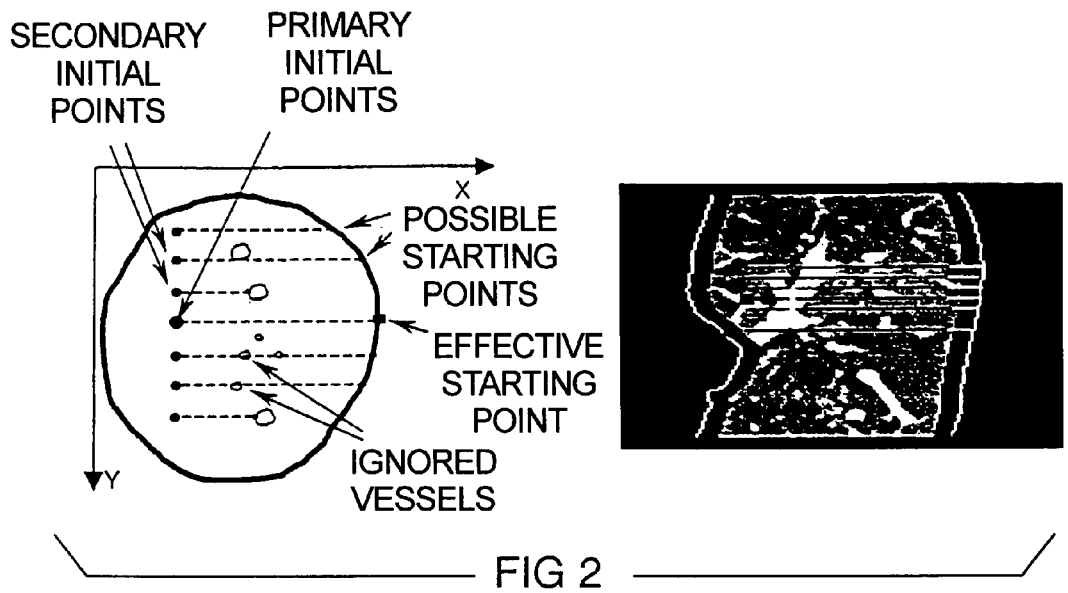
FIG. 2 is a diagram illustrating the determination of the starting point for the contour finding algorithm.

The user sets a primary starting point in both lungs. Proceeding from these, a number of secondary starting points, for example seven secondary starting points, is determined, whereby three lie in y-direction above and three lie in y-direction below the primary starting point (FIG. 2).

For example, the spacing between the starting points in the y-direction respectively amounts to five pixels; and x-coordinates correspond to those of the primary starting point. Seven possible starting points are determined from the starting points in exactly horizontal direction, i.e. x-direction. The search for a possible starting point in the x-direction in each lung proceeding from the respective starting point in the direction toward the edge of the image. A point is defined as starting point whose CT value is at most equal to the aforementioned threshold and that is followed by a number of n pixels, for example n=5 pixels, that lie above the threshold. The available starting point having the greatest distance in the x-direction from the appertaining starting point is utilized as the effective starting point of the contour finding, i.e., the outermost pixel that still lies within the CT value range for pulmonary parenchyma is selected as effective starting point.

The standard algorithm with n=1 would occasionally fail in slices having a high density of vessels filled with contrast agents because all search paths end at vessel walls and not at the pleura. The assumption of an average vessel diameter of n pixels, for example n=5, reduces the sensitivity of the algorithm. The starting point having the greatest distance in x-direction from the appertaining initial point is utilized as the starting point of the contour finding.

Figure 3:
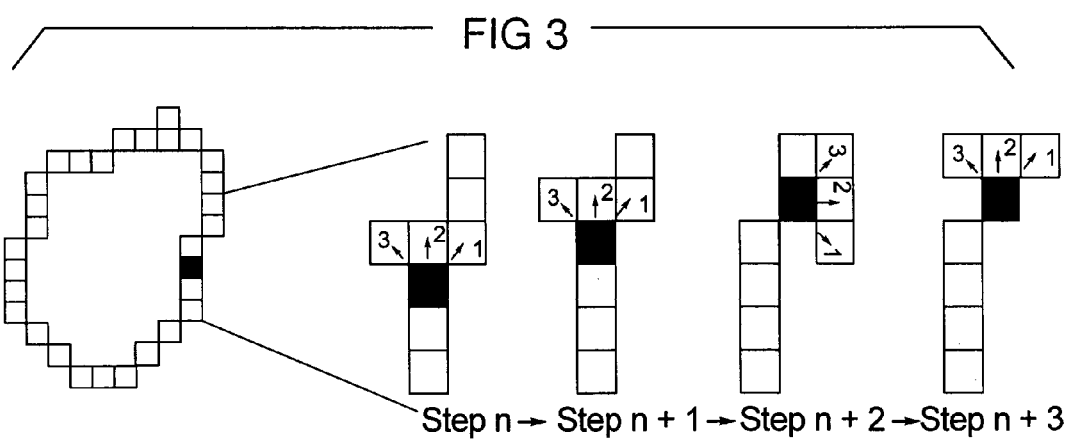
FIG. 3 is a diagram illustrating the contour finding algorithm.

The standard algorithm was also adapted in view of the actual contour finding of the lung (FIG. 3). The search for contour points proceeds counter-clockwise, proceeding from the effective starting point found in the way set forth above. The algorithm always considers the first three neighboring points in search direction and first determines the pixel having a value below the threshold as the next contour point. When the first of the three neighboring points is detected as a contour point, the search direction is modified to −90° compared to the original search direction. If none of the three pixels meets the criterion, the search direction is modified to +90° relative to the original search direction. In all other instances, the original search direction is retained unmodified. The algorithm is allowed to reverse the search direction and thus return on its own track. If the number of iterations exceeds a predetermined value, the contour search is aborted.

Figure 4:
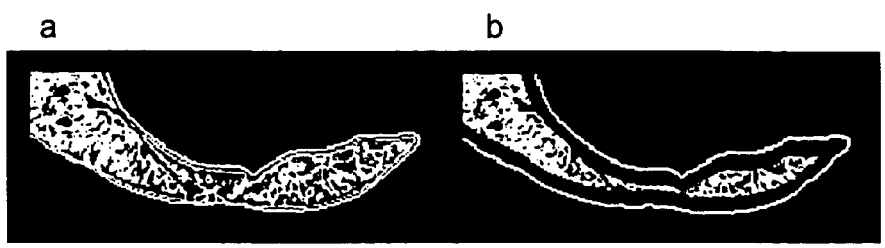
FIG. 4 is a diagram illustrating the erosion of pixels lying on the contour that has been found, wherein a) shows the condition before the erosion, and b) shows the condition after the erosion of five layers of pixel.

A binary segmentation mask is produced on the basis of the acquired (extracted) contour. In order to eliminate pixels that belong to the pleura for this purpose, the segmentation mask is eroded in five layers, whereby the erosions employ the principle of the "four connected neighbors" as structuring element (FIG. 4). This principle is described in John, C. Russ, "The Image Processing Handbook", Springer Verlag, 1999.

When processing stacks of images, the middle position of each lung is derived from the segmentation mask and is employed as the primary initial point of the segmentation of the next image. The segmentation then automatically progresses until the entire stack has been processed.

In order to edit the data for the following smoothing operation, larger vessel structures and air paths are removed from the image during the course of the vessel elimination on the basis of HU value selection. A lower threshold $HU_B$ and an upper threshold $HU_V$ are prescribed; pixels below $HU_B$ are identified as air paths, for example bronchia, and pixels above $HU_V$ are identified as vessels.

Figure 5:
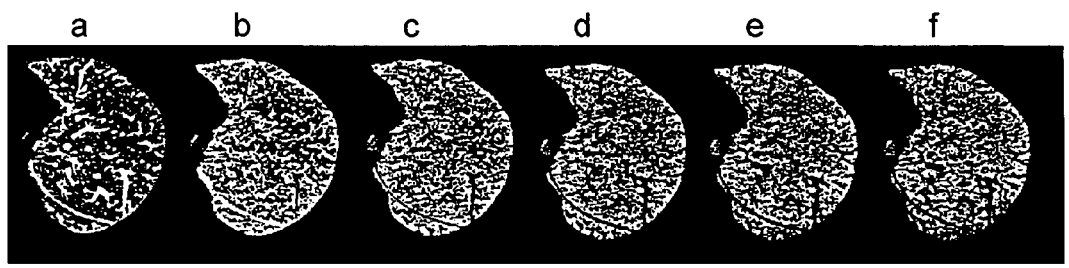
FIG. 5 shows the influence of the parameters underlying the vessel elimination, whereby all images are windowed with a central value of 800 HU and a width of 300 HU, and wherein
  a) represents the original image,
  b) represents 8% removed pixels given $HU_B = -990$, $HU_V = -655$,
  c) represents 18% removed pixels given $HU_B = -990$, $HU_V = -783$,
  d) represents 28% removed pixels given $HU_B = -990$, $HU_V = -827$,
  e) represents 38% removed pixels given $HU_B = -990$, $HU_V = -849$,
  f) represent 48% removed pixels given $HU_B = -990$, $HU_V = -864$.

In order to obtain an optimum image impression, a balance must be found between the two objectives of removing optimally all vessels and retaining optimally many pulmonary pixels in the image. The optimum value for $HU_V$ thereby differs from patient to patient and can even change within one and the same patient. A definition of $HU_V$ as percentage is thus more universally valid, for which reason a combination of threshold-based and percentage-based procedure is applied. Investigations have shown that the maximum number of removed pulmonary pixels is expediently limited to 28% of all pulmonary pixels, whereby $HU_V$ is calculated such that the 28% limit is adhered to, whereas a fixed value of −990 HU is expedient for $HU_B$ (FIG. 5).

Figure 6:
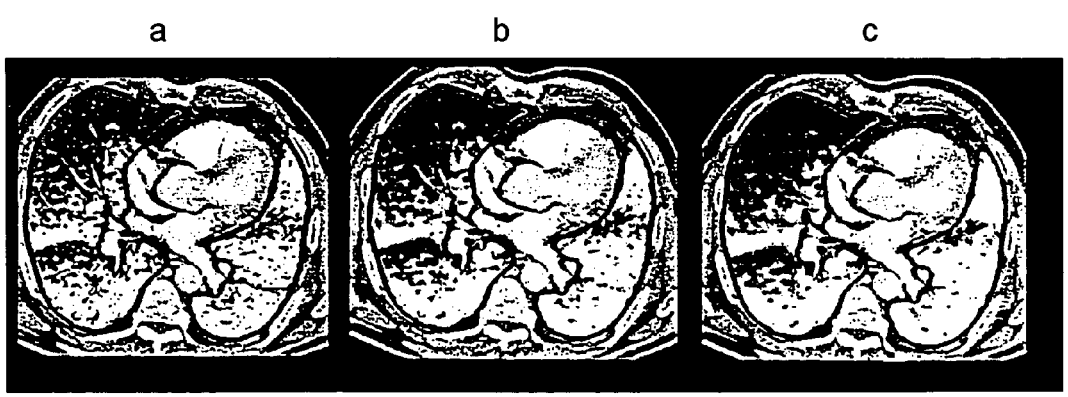
FIG. 6 shows the influence of the diameter of the filter core in the smoothing operation, wherein the diameter for a) amounts to seven pixels corresponding to 4.9 mm, the diameter for b) amounts to 9 pixels corresponding to 6.4 mm and the diameter for c) amounts to 11 pixels corresponding to 7.8 mm.

The segmented image is subjected to a smoothing operation that is reformatted by linear interpolation during the course of an adaptive filtering in order to obtain isotropic pixel spacings. In detail, an adaptive sliding average value filtering is applied upon employment of an isotropic filter kernel (circular in the two-D case and spherical in the three-D case). When, as in the case of the described exemplary embodiment, no pulmonary parenchyma structures below a size of 5 mm are to be interpreted, a filter kernel having a diameter of 5 mm is preferably utilized (FIG. 6). In standard CT images, this corresponds to seven pixels.

Given application of the filter, the middle pixel of the current kernel is replaced by the average value of all pixels of the respective kernel. Pixels that were removed in the preceding operations (segmentation, erosion, vessel elimination) are defined as invalid and do not contribute to the formation of the average value.

Figure 7:
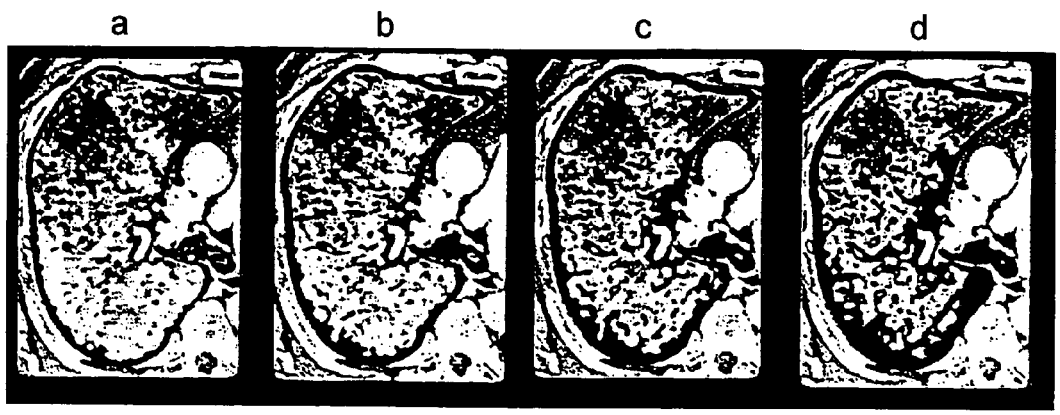
FIG. 7 shows the influence of the vessel factor for a vessel factor of a) 5%, b) 20%, c) 35%, and d) 50%.

The minimum proportion of valid pixels that must be present in a kernel in order to be able to produce a valid result of the formation of the average value is defined by the user. This minimum proportion is prescribed as a percentage, this being referred to below as the vessel factor. If the proportion lies below the limit value, the middle pixel is set as being invalid. Since all invalid pixels are replaced in the last processing step by the corresponding pixels of the original image, the vessel factor defines how many vessel structures and air paths will appear in the processed pulmonary parenchyma region. A vessel factor 28% is preferably employed (FIG. 7).

When stacks of images are processed, a spherical 3D filter kernel is applied—as already mentioned—this acquiring seven successive images of the stack, accordingly, in the case of a diameter of seven pixels.

The implementation of the filter algorithm advantageously makes use of a fast numerical convolution algorithm. It is described below for a 2D filter and can be easily expanded to 3D.

All pixels of the image that are invalid or lie outside the detected contour are set to 0. The image matrix and its binary mask are then separately convoluted. The convolution of the binary mask yields the plurality of valid pixels corresponding to the position of the value in the matrix. The vessel factor is taken into consideration in that the corresponding threshold is applied to the matrix, and all values below the threshold are set to 0. In order to obtain the filtered image, the convoluted image is divided by the convoluted mask, whereby the division is implemented element for element. When an element of the convoluted binary mask is 0, the result is set to invalid status.

In order to facilitate the illustration of the contrast agent enhancement in the pulmonary parenchyma, the resulting image is presented in false colors in a spectral color scale, whereby a color scale covering the spectral colors, i.e. from red through violet is applied. The color coding ensuing for the purpose of the false color presentation is controlled by a windowing analogous to the gray scale value presentation. The parameters of the window are determined heuristically, i.e. the histogram of the pulmonary parenchyma pixels is analyzed for automatically determining the parameters. The center of gravity of the histogram distribution is employed as the central value of the windowing, and the width of the window is set to a value of approximately 100 HU.

The resulting image of the pulmonary parenchyma is superimposed on the original image. A separate windowing of the gray scale values and the parts of the image presented in color can thereby ensue. The underlying original image is essential for the spatial orientation in the data set.

Figure 8:
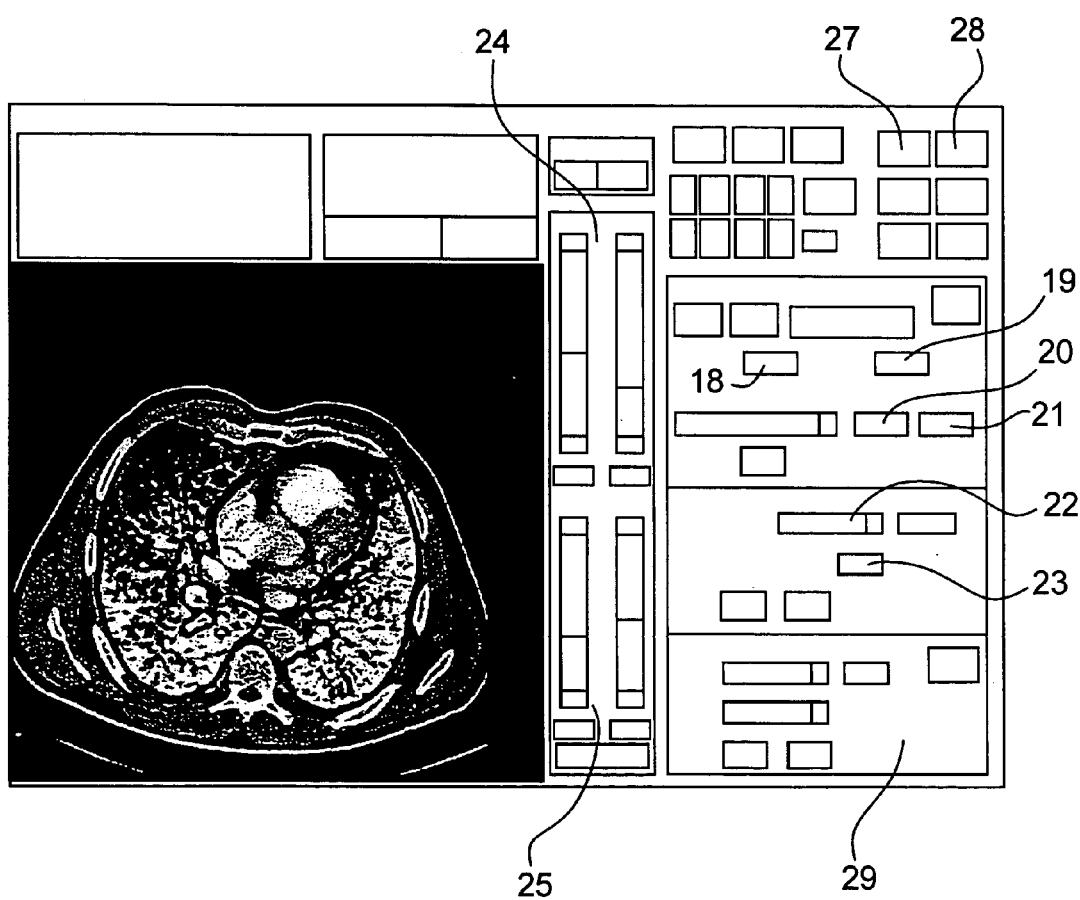
FIG. 8 shows the user interface of the CT apparatus of FIG. 1.

The user interface of the CT apparatus according to FIG. 1 shown in FIG. 8, which is used for controlling the inventive method, comprises a region with operating elements in addition to a region serving the purpose of image presentation.

In detail, the operating elements are provided for the segmentation, whereby the threshold for the segmentation can be set with the operating element 18, the number of (primary and secondary) initial points can be set with the operating element 19, the value for $HU_B$ can be set with the operating element 20, and the vessel factor can be set with the operating element 21.

A region having operating elements for the smoothing operation is also provided, whereby the filter kernel together with diameter of the filter kernel is selected with the operating element 22, and the number of images to be acquired with the filter kernel is set with the operating element 23 when processing a stack of images.

Further, two regions 24 and 25 are provided that contain operating elements for setting the parameters of the windowing of the black-white and color picture parts.

Operating elements 27 and 28 provide the possibility of switching between black-white and false color presentation.

Finally, a region 29 is present that contains operating elements that serve the purpose of subtracting two images processed according to the above-described method from one another, one of which having been acquired without and one with contrast agent.

Critical data sets were subjected to the inventive image processing that were registered with chest examinations, these having been implemented because of clinical suspicion of PE. Non-ionic contrast agent (Ultravist 370, Schering, Berlin, Germany) was thereby intravenously administered with a contrast agent injector (CT 9000 Digital Injection System, Liebel-Flarsheim, Cincinnati, Ohio). A total of 120 cm$^3$ contrast agent were thereby administered given a flow rate of 3 cm$^3$/s, followed by a table salt solution (total of 30 cm$^3$ at 3 cm$^3$/s). The start delay between the beginning of the contrast agent administration and the beginning of the registration amounted to 30 seconds for all patients. The registration of the images ensued with a commercially obtainable multi-line CT apparatus (Somatom Volume Zoom; Siemens AG Forchheim, Germany). The exposure parameters were 140 kV and 100 mAs upon employment of a narrow collimation of 4×1 mm given a pitch of 1.75. The entire chest was therefore capable of being examined during a single pause in respiration lasting 21 seconds. No further examinations in later respiratory pauses were required. The initial images acquired in this way were retrospectively reconstructed for a slice thickness of 1.25 mm and a reconstruction increment of 0.8 mm and were exported for image processing onto a PC (Pentium III, 600 MHz).

In order to demonstrate the effect of the inventive method, images of a patient without pathological change (FIG. 9) and of a patient with documented PE (FIG. 10) are respectively presented in axial orientation, whereby the regions of high density, i.e. high contrast agent enhancement, are presented red in practice and the regions of lower density, i.e. essentially without contrast agent enhancement are presented violet. Due to the black-white illustration of FIGS. 9 and 10, high-density regions therein are referenced H and the regions with low density are referenced by arrows reference L.

Figure 9:
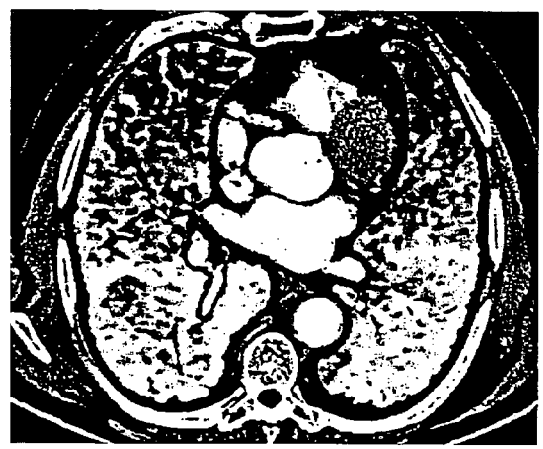
FIG. 9 shows an axial image of the lung of a patient without diagnosis in false color presentation.

FIG. 9 shows an axial image at the level of the left atrium after the intravenous administration of contrast agent. A complete contrast agent enhancement is present in all pulmonary vessels. No perfusion deficits can be seen in the illustration of the pulmonary parenchyma. Neither regions of especially high nor especially low density can be recognized; corresponding arrows are therefore lacking.

Figure 10:
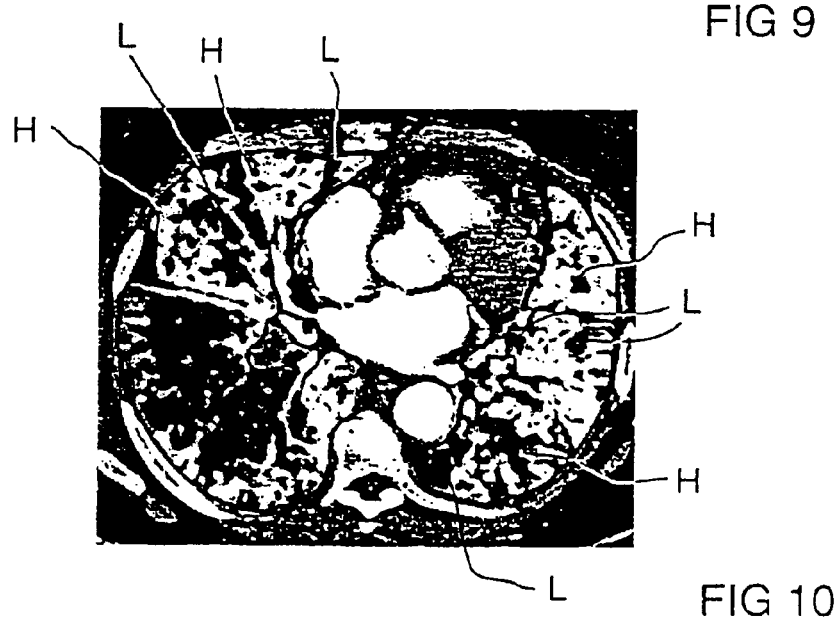
FIG. 10 is an axial image of the lung of a patient suffering from PE in a false color presentation.

FIG. 10 shows a number of arteries form closures due to thromboses. Correspondingly, regions of increased density due to blocked contrast agent and regions of reduced density due to low blood flow occur, these being identified by corresponding arrows.

It is thus clear that an improved diagnosis is possible by means of the inventive method. Both ends of the color scale, i.e. red and violet, can indicate a pathological situation in the pulmonary parenchyma. Red regions are regions of increased density and, for example, be caused by atelectases. Violet regions are regions of reduced density that can be possibly caused by reduced blood flow and, thus, reduced contrast agent enhancement.

Although modifications and changes may be suggested by those skilled in the art, it is in the intention of the inventors to embody within the patent warranted hereon all changes and modifications as reasonably and properly come within the scope of their contribution to the art.

We claim:

1. A method for processing a computed tomography image comprising the steps of:
   obtaining a computed tomography image of a lung of a subject with contrast agent administered to the subject so as to affect said image, said image being comprised of pixels each having a Houndsfield Unit (HU) value associated therewith and each having a gray scale associated therewith dependent on the HU value thereof;
   determining pixels representing pulmonary parenchyma in said image, as pulmonary parenchyma pixels; and
   generating a processed image by presenting all of said pulmonary parenchyma pixels in false colors respectively corresponding to different HU values, and presenting remaining pixels in said image in said gray scale values.

2. A method as claimed in claim 1 wherein the step of determining the pulmonary parenchyma pixels comprises applying a contour finding algorithm to said image and thereby separating said pulmonary parenchyma pixels from said remaining pixels.

3. A method as claimed in claim 1 comprising determining said pulmonary parenchyma pixels, together with pixels representing bronchia and vessels, based on said HU values, and removing said pixels representing bronchia and vessels from said pulmonary parenchyma pixels.

4. A method as claimed in claim 3 wherein said pulmonary parenchyma pixels and said pixels representing bronchia and vessels comprise a totality of pixels, and comprising removing only a portion of said totality of pixels which does not exceed a predetermined maximum percentage of said totality of pixels.

5. A method as claimed in claim 4 comprising classifying the removed pixels as invalid pixels.

6. A method as claimed in claim 5 comprising subjecting a region of said image containing said pulmonary parenchyma pixels to a smoothing operation and excluding said invalid pixels from said smoothing operation.

7. A method as claimed in claim 6 comprising conducting a sliding averaging of said pixels in said region containing said pulmonary parenchyma pixels as said smoothing operation.

8. A method as claimed in claim 6 comprising selecting only a plurality of pixels, from among said pixels in said region containing said pulmonary parenchyma pixels, for smoothing in said smoothing operation.

9. A method as claimed in claim 8 comprising identifying a middle pixel in said plurality of pixels selected for said smoothing operation, and conducting said smoothing operation by generating an average value of said plurality of pixels selected for said smoothing operation, referenced to said middle pixel.

10. A method as claimed in claim 9 comprising designating a minimum proportion of valid pixels among said plurality of pixels selected for said smoothing operation, and setting said middle pixel to an invalid status if said minimum proportion is not reached.

11. A method as claimed in claim 5 comprising superimposing said pulmonary parenchyma pixels presented in false colors on said pixels presented in gray scale values, and replacing any pixels classified as invalid with corresponding pixels of said image in gray scale values.

12. A method as claimed in claim 1 comprising subjecting said pulmonary parenchyma pixels presented in false colors and said remaining image regions presented in said gray scale values to respectively independent windowing operations.

13. A method as claimed in claim 12 comprising windowing the pulmonary parenchyma pixels presented in false colors dependent on a histogram of said pulmonary parenchyma pixels.

14. A method as claimed in claim 13 wherein said histogram has a center of gravity, and employing said center of gravity as a central value in said windowing of said pulmonary parenchyma pixels, and setting a width of a window in said windowing of said pulmonary parenchyma pixels to a fixed value of 100 HU.

15. A method as claimed in claim 1 comprising obtaining a plurality of computed tomography images of said lung comprising, in combination, volume data from said subject, and for each of said images in said plurality of images, determining said pulmonary parenchyma pixels and generating a processed image wherein the pulmonary parenchyma pixels are presented in false colors and wherein the remaining image regions are presented in said gray scale values.

16. A method as claimed in claim 15 comprising conducting a multi-planar image reconstruction of said volume data comprised of said plurality of images.

17. A method as claimed in claim 1 wherein said computed tomography image is a first computed tomography image and wherein said processed image is a first processed image, and comprising the additional steps of:
obtaining a second computed tomography image of said lung of said subject without said contrast agent effecting said second computed tomography image, said second computed tomography image being comprised of a plurality of pixels respectively having gray scale values associated therewith, and containing pixels representing pulmonary parenchyma, as pulmonary parenchyma pixels;
generating a second processed image by presenting all of said pulmonary parenchyma pixels in said second computed tomography image in said false colors and presenting said, remaining image regions in said second computed tomography image in said gray scale values; and
subtracting said first processed image and said second processed image from each other.

18. A computed tomography apparatus for processing a computed tomography image comprising:
a scanner with a contrast agent injector for obtaining a computed tomography image of a lung of a subject with contrast agent administered to the subject so as to effect said image, said image being comprised of pixels each having a Houndfield Unit (HU) value associated therewith and each having a gray scale associated therewith dependent on the HU value thereof;
a processor for determining pixels representing pulmonary parenchyma in said image, as pulmonary parenchyma pixels;
a display connected to said processor; and
said processor generating a processed image wherein all of said pulmonary parenchyma pixels are presented in false colors respectively corresponding to different HU values, and remaining pixels in said image are presented in said gray scale values and causing said processed image to be displayed at said display.

19. A computed tomography apparatus as claimed in claim 18 wherein said computed tomography image is a first computed tomography image and wherein said processed image is a first processed image, and wherein:
said scanner obtains a second computed tomography image of said lung of said subject without said contrast agent affecting said second computed tomography image, said second computed tomography image being comprised of a plurality of pixels respectively having gray scale values associated therewith, and containing pixels representing pulmonary parenchyma, as pulmonary parenchyma pixels;
said processor generating a second processed image wherein all of said pulmonary parenchyma pixels in said second computed tomography image are presented in said false colors and remaining image regions in said second computed tomography image are presented in said gray scale values; and
said processor subtracting said first processed image and said second processed image from each other to obtain a resultant image, said processor causing said resultant image to be displayed on said display.

20. A computed tomography apparatus as claimed in claim 18 comprising a user interface, including said display, connected to said processor, said user interface having an actuatable operating element for implementing the determination of pixels representing pulmonary parenchyma in said image and the display of said processed image.

21. A workstation for processing a computed tomography image of a lung of a subject with contrast agent administered to the subject so as to affect said image, said image being comprised of pixels each having a Houndfield Unit (HU) value associated therewith and each having a gray scale value associated therewith dependent on the HU value thereof, said workstation comprising:
a processor for determining pixels representing pulmonary parenchyma in said image, as pulmonary parenchyma pixels;
a display connected to said processor; and
said processor generating a processed image wherein all of said pulmonary parenchyma pixels are presented in false colors respectively corresponding to different HU values, and remaining pixels in said image are presented in said gray scale values, and said processor causing said processed image to be displayed on said display.

22. A workstation as claimed in claim 21 wherein said computed tomography image is a first computed tomography image and wherein said processed image is a first processed image, and wherein said processor is supplied with a second computed tomography image of said lung of said subject without said contrast agent affecting said second computed tomography image, said second computed tomography image being comprised of a plurality of pixels respectively having gray scale values associated therewith, and containing pixels representing pulmonary parenchyma, as pulmonary parenchyma pixels, and wherein said processor generates a second processed image wherein all of said pulmonary parenchyma pixels in said second computed tomography image are presented in said false colors and remaining image regions in said second computed tomography image are presented in said gray scale values, and wherein said processor subtracts said first processed image and said second processed image from each other to obtain a resultant image and causes said resultant image to be displayed on said display.

23. A workstation as claimed in claim 21 comprising a user interface, including said display, connected to said processor, said user interface having an actuatable operating element for implementing the determination of pixels representing pulmonary parenchyma in said image and the display of said processed image.

* * * * *